(12) United States Patent
Davidsen

(10) Patent No.: US 11,090,027 B2
(45) Date of Patent: Aug. 17, 2021

(54) METHODS, APPARATUSES, AND SYSTEMS FOR COUPLING A FLEXIBLE TRANSDUCER TO A SURFACE

(71) Applicant: KONINKLIJKE PHILIPS N.V., Eindhoven (NL)

(72) Inventor: Richard Edward Davidsen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 179 days.

(21) Appl. No.: 15/735,376

(22) PCT Filed: Jun. 17, 2016

(86) PCT No.: PCT/IB2016/053599
§ 371 (c)(1),
(2) Date: Dec. 11, 2017

(87) PCT Pub. No.: WO2017/001962
PCT Pub. Date: Jan. 5, 2017

(65) Prior Publication Data
US 2018/0168544 A1    Jun. 21, 2018

Related U.S. Application Data

(60) Provisional application No. 62/186,412, filed on Jun. 30, 2015.

(51) Int. Cl.
*A61B 8/00* (2006.01)
*A61B 8/08* (2006.01)

(52) U.S. Cl.
CPC ............ *A61B 8/4227* (2013.01); *A61B 8/403* (2013.01); *A61B 8/429* (2013.01); *A61B 8/4254* (2013.01); *A61B 8/4263* (2013.01); *A61B 8/4281* (2013.01); *A61B 8/4483* (2013.01); *A61B 8/08* (2013.01); *A61B 8/4427* (2013.01)

(58) Field of Classification Search
None
See application file for complete search history.

(56) References Cited

U.S. PATENT DOCUMENTS

| | | |
|---|---|---|
| 3,552,382 A | 1/1971 | Mount |
| 3,587,561 A | 6/1971 | Ziedonis |
| 5,680,863 A | 10/1997 | Hossack et al. |
| 5,735,282 A | 4/1998 | Hossack |
| 5,840,036 A | 11/1998 | Voith |
| 6,306,090 B1 | 10/2001 | Wilk |
| 6,443,896 B1 | 9/2002 | Detmer |

(Continued)

FOREIGN PATENT DOCUMENTS

| | | |
|---|---|---|
| CN | 101330874 A | 12/2008 |
| EP | 2710961 A1 | 3/2014 |

(Continued)

*Primary Examiner* — Joseph M Santos Rodriguez

(57) ABSTRACT

Systems, methods, and apparatuses for coupling a flexible transducer to an object are described. A transducer positioning device may include an inflatable bladder and a strap. The inflatable bladder may apply a force to a transducer array to maintain its position against the object when inflated. The strap may hold the bladder against the transducer array. Once in place, the bladder may be inflated with a fluid.

15 Claims, 6 Drawing Sheets

(56) References Cited

U.S. PATENT DOCUMENTS

| | | |
|---|---|---|
| 6,530,885 B1 | 3/2003 | Entrekin et al. |
| 7,033,321 B1 * | 4/2006 | Sarvazyan ............. A61B 5/411 |
| | | 600/449 |
| 8,649,185 B2 | 2/2014 | Wodnicki et al. |
| 8,912,709 B2 | 12/2014 | Pollock et al. |
| 2006/0106310 A1 | 5/2006 | Lo et al. |
| 2007/0066897 A1 | 3/2007 | Sekins et al. |
| 2008/0306414 A1 | 12/2008 | Petruzzello et al. |
| 2008/0312562 A1 | 12/2008 | Routh et al. |
| 2009/0024034 A1 | 1/2009 | Moreau-Gobard et al. |
| 2010/0204577 A1 | 8/2010 | Sekins et al. |
| 2012/0095343 A1 | 4/2012 | Smith et al. |
| 2013/0158418 A1 | 6/2013 | Mizukami |

FOREIGN PATENT DOCUMENTS

| | | |
|---|---|---|
| JP | S5775640 A | 5/1982 |
| JP | 59114994 A | 7/1984 |
| JP | 10258053 A | 9/1998 |
| JP | 2013144098 A | 7/2013 |
| JP | 2013158347 A | 8/2013 |
| JP | 2013539715 A | 10/2013 |
| WO | 9847428 A1 | 10/1998 |
| WO | 2008137030 A1 | 5/2008 |
| WO | 2011089160 A2 | 7/2011 |

\* cited by examiner

METHODS, APPARATUSES, AND SYSTEMS FOR COUPLING A FLEXIBLE TRANSDUCER TO A SURFACE

This application is the U.S. National Phase application under 35 U.S.C. § 371 of International Application No. PCT/IB2016/053559, filed on Jun. 17, 2016, which claims the benefit of Provisional Application Ser. No. 62/186,412, filed Jun. 30, 2015. These applications are hereby incorporated by reference herein.

BACKGROUND

Large, flexible ultrasound transducer arrays may enable new ultrasound applications such as emergency medicine and user-independent imaging. The surface area of a flexible transducer array may be greater than the surface area of a conventional rigid ultrasound transducer array included in a handheld ultrasound probe. The array may flex such that it conforms to a surface of a patient's body or another object.

Achieving and maintaining consistent contact with the surface across the entire flexible array may be difficult. During conventional ultrasound imaging, contact is maintained by a sonographer holding the ultrasound probe. The sonographer applies a force with the probe to the surface of the patient or object to be imaged to maintain acoustical coupling between the transducer array and the surface. For flexible transducer arrays, the array may be too large for a sonographer to hold in place by hand. In some cases, the array may need to stay in place for an extended period of time, making it impractical for a sonographer to hold the array in place.

SUMMARY

An example apparatus according to an embodiment of the disclosure may include a transducer array that may include a first surface and a second surface opposite the first surface, the second surface may be configured to be placed against an object to be imaged, a bladder adjacent the first surface of the transducer array, the bladder may be configured to be inflated by a fluid, and a strap that may be configured to wrap around the bladder and the object, wherein the strap and the bladder may be configured to maintain a force against the first surface of the transducer array.

An example ultrasound system according to an embodiment of the disclosure may include a flexible transducer array that may be configured to transmit an ultrasound signal, a beamformer coupled to the flexible transducer array, the beamformer may be configured to control the ultrasound signal, a transducer positioning device that may be configured to maintain a position of the flexible transducer array against an object, the transducer positioning device may include: a bladder that may be configured to be inflated; and a strap that may be configured to maintain the bladder in contact with the flexible transducer array.

An example method according to an embodiment of the disclosure may include applying an ultrasound transducer to a surface of an object; applying a bladder to a surface of the ultrasound transducer distal to the object; applying a strap to the bladder and the object; and inflating the bladder.

DETAILED DESCRIPTION

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system.

The following detailed description is therefore not to be taken in a limiting sense, and the scope of the present system is defined only by the appended claims. The leading digit(s) of the reference numbers in the figures herein typically correspond to the figure number, with the exception that identical components which appear in multiple figures are identified by the same reference numbers. Moreover, for the purpose of clarity, detailed descriptions of certain features will not be discussed when they would be apparent to those with skill in the art so as not to obscure the description of the present system.

Large, flexible transducer arrays may enable applications of ultrasound imaging and/or therapy. For example, a flexible transducer array may be wrapped around an object and areas of interest may be imaged without requiring a sonographer to manipulate an ultrasound probe. This may allow a clinician with minimal training to obtain ultrasound images. For example, the clinician may be an emergency medical technician (EMT) imaging a victim of a motor vehicle accident to determine if the victim is suffering from internal bleeding while at the site of the accident or during transport to the hospital. The EMT may apply the flexible transducer array to the victim's torso. The large transducer array may allow the EMT to acquire images of the victim's various internal organs (e.g., liver, spleen) without moving the transducer array after it has been applied. An ultrasound imaging system coupled to the flexible transducer array may automatically scan the victim's torso across the array using electronic beam steering and/or other techniques. The EMT may use the acquired images to make treatment decisions and/or provide the images to the hospital on arrival.

Figure 1:
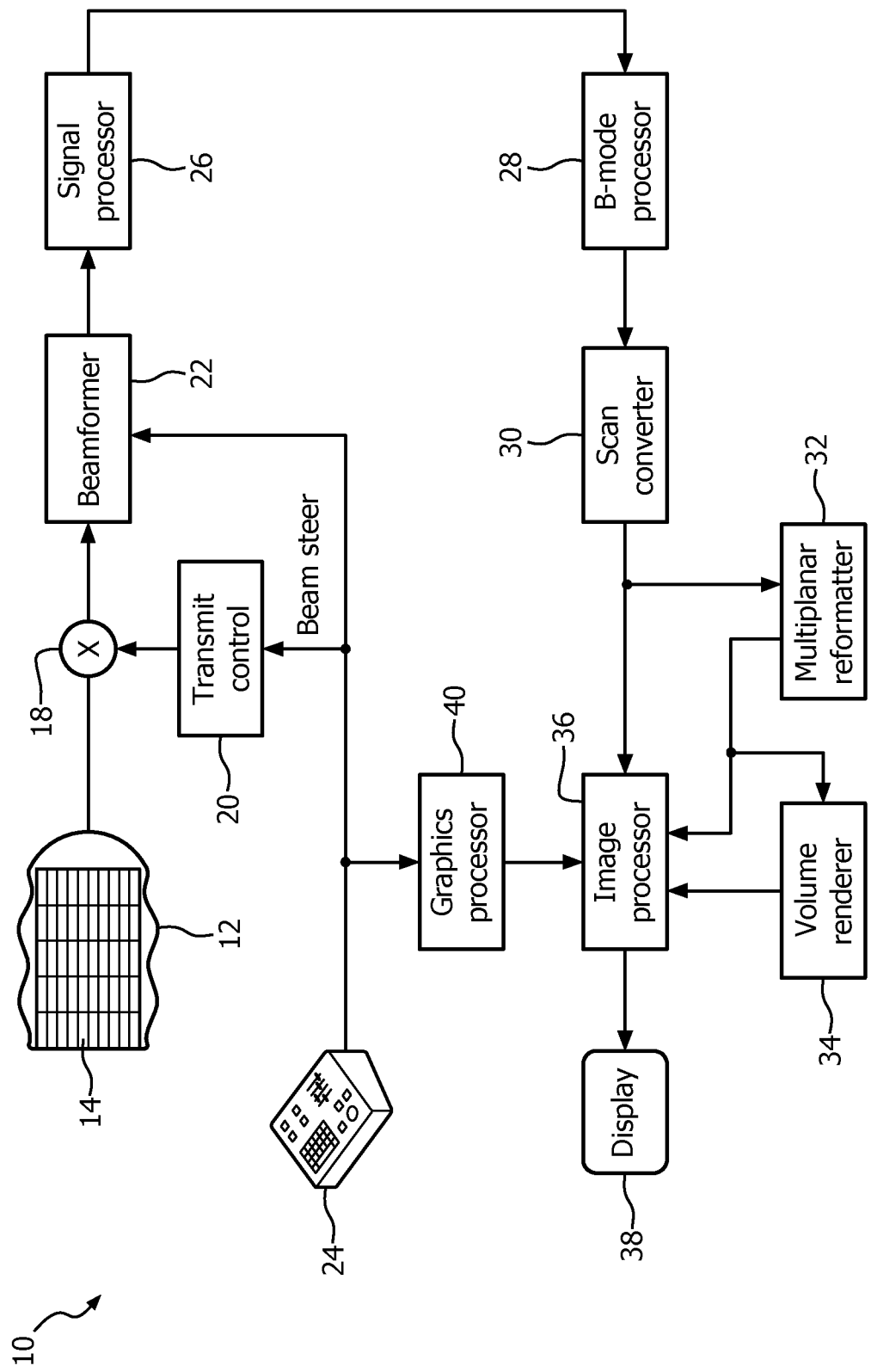
FIG. 1 is a block diagram of an ultrasound imaging system according to an embodiment of the disclosure.

Referring to FIG. 1, an ultrasound imaging system 10 constructed in accordance with the principles of the present invention is shown in block diagram form. The ultrasound imaging system 10 may be used to implement the ultrasound imaging system described in the previous example. In the ultrasonic diagnostic imaging system of FIG. 1, an ultrasound probe 12 includes a transducer array 14 for transmitting ultrasonic waves and receiving echo information. A variety of transducer arrays are well known in the art, e.g., linear arrays, convex arrays or phased arrays. The transducer array 14, for example, can include a two dimensional array (as shown) of transducer elements capable of scanning in both elevation and azimuth dimensions for 2D and/or 3D imaging. The transducer array may be a flexible array in some embodiments. The transducer array 14 is coupled by the probe cable to a transmit/receive (T/R) switch 18, which switches between transmission and reception and protects a main beamformer 22 from high energy transmit signals. The main beamformer 22 may control transmission and reception of signals by the transducer elements in the transducer array 14. In some embodiments, the T/R switch 18 and other elements in the system can be included in the transducer probe 12 rather than in a separate ultrasound system base. The transmission of ultrasonic beams from the transducer array 14 under control of the main beamformer 22 is directed by the transmit controller 20 coupled to the T/R switch 18 and the beamformer 22, which receives input from the user's operation of the user interface or control panel 24. One of the functions controlled by the transmit controller 20 is the direction in which beams are steered. Beams may be steered straight ahead from (orthogonal to) the transducer array, or at different angles for a wider field of view.

In some embodiments, the transducer array 14 may be coupled to a microbeamformer (not shown) included in the probe 12, or adjacent to the probe 12, which may at least partially control transmission and reception of signals by the transducer elements in the transducer array 14. In these embodiments, the transmission of ultrasonic beams from the transducer array 14 under control of the microbeamformer is directed by the transmit controller 20 coupled to the T/R switch 18 and the beamformer 22, which receives input from the user's operation of the user interface or control panel 24. The microbeamformer may partially beamform signals, and the partially beamformed signals produced by the microbeamformer are coupled to a main beamformer 22 where the partially beamformed signals from individual patches of transducer elements are combined into a fully beamformed signal. The microbeamformer may be implemented as a flexible circuit coupled to the transducer array 14. The microbeamformer may be implemented in a flexible circuit that also includes the transducer array 14, in some embodiments. Alternatively, the microbeamformer may be implemented in a rigid or semi-rigid printed circuit board (PCB) coupled to the transducer array 14. For example, the PCB may be electrically coupled to a flexible circuit including the transducer array 14 and adhesively coupled to a periphery of the flexible circuit proximate to the transducer array 14. In some embodiments, the microbeamformer is located elsewhere in the probe 12 and electrically coupled to the transducer array 14 (e.g., wires). Other configurations of the microbeamformer coupled to the transducer array 14 may also be implemented. For example, in some embodiments, the microbeamformer may be a beamformer that fully beamforms the signals from the transducer array 14, and imaging data from the beamformer to the signal processor 26.

The beamformed signals are coupled to a signal processor 26. The signal processor 26 can process the received echo signals in various ways, such as bandpass filtering, decimation, I and Q component separation, and harmonic signal separation. The signal processor 26 may also perform additional signal enhancement such as speckle reduction, signal compounding, and noise elimination. The processed signals are coupled to a B mode processor 28, which can employ amplitude detection for the imaging of structures in the body. The signals produced by the B mode processor are coupled to a scan converter 30 and a multiplanar reformatter 32. The scan converter 30 arranges the echo signals in the spatial relationship from which they were received in a desired image format. For instance, the scan converter 30 may arrange the echo signal into a two dimensional (2D) sector-shaped format, or a pyramidal three dimensional (3D) image. The multiplanar reformatter 32 can convert echoes which are received from points in a common plane in a volumetric region of the body into an ultrasonic image of that plane, as described in U.S. Pat. No. 6,443,896 (Detmer). A volume renderer 34 converts the echo signals of a 3D data set into a projected 3D image as viewed from a given reference point, e.g., as described in U.S. Pat. No. 6,530,885 (Entrekin et al.) The 2D or 3D images are coupled from the scan converter 30, multiplanar reformatter 32, and volume renderer 34 to an image processor 36 for further enhancement, buffering and temporary storage for display on an image display 38. The graphics processor 36 can generate graphic overlays for display with the ultrasound images. These graphic overlays can contain, e.g., standard identifying information such as patient name, date and time of the image, imaging parameters, and the like. For these purposes the graphics processor receives input from the user interface 24, such as a typed patient name. The user interface can also be coupled to the multiplanar reformatter 32 for selection and control of a display of multiple multiplanar reformatted (MPR) images The transducer array 14 may be continuously flexible across the entire array or it may be made up of a number of smaller rigid or semi-rigid sub-arrays coupled together with flexible joints between the sub-arrays. A transducer array including multiple sub-arrays flexibly coupled together may be referred to as a piecewise flexible array.

Figure 2B:
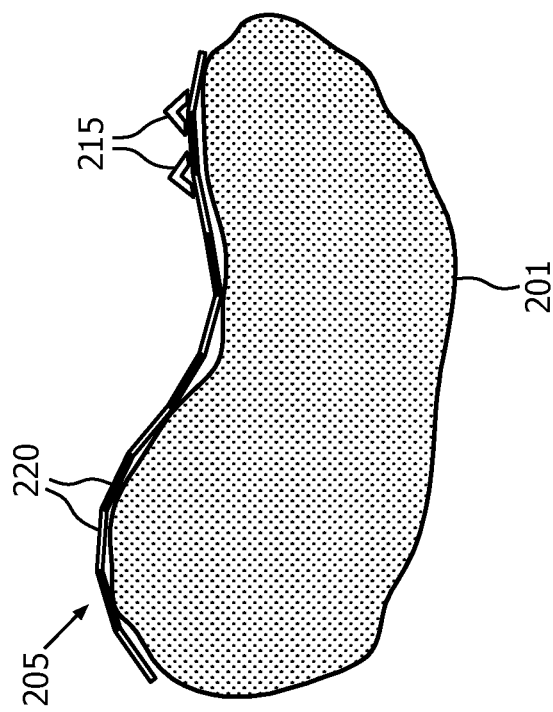
FIG. 2B is an illustration of a piecewise flexible transducer array according to an embodiment of the disclosure.
Figure 2A:
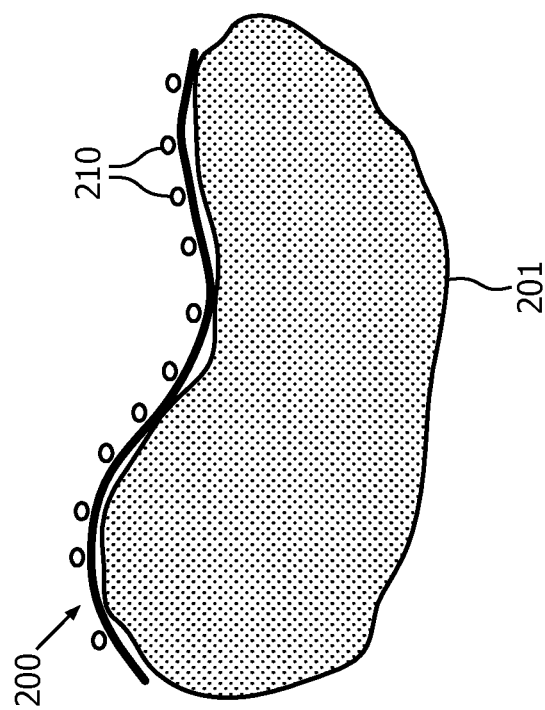
FIG. 2A is an illustration of a continuously flexible transducer array according to an embodiment of the disclosure.

FIG. 2A illustrates a continuously flexible array 200 on an object 201 and FIG. 2B illustrates a piecewise flexible array 205 on an object 201, respectively, according to embodiments of the disclosure. Flexible arrays 200, 205 may be used to implement transducer array 14 shown in FIG. 1 in some embodiments.

The continuously flexible array 200 illustrated in FIG. 2A may include multiple transducer elements (not shown) coupled to and/or embedded in a flexible substrate. For example, the transducer elements may be included in and/or on a flexible printed circuit. The flexible circuit may be able to bend, fold and/or twist. This may allow the flexible circuit to curve around another component and/or conform to a surface. The degree of flexibility of the flexible circuit may be determined, at least in part, by materials chosen for the flexible circuit (e.g. films, conductive elements, circuit components). The flexible circuit may include an insulating polymer film with conductive elements (e.g., wires) applied on one surface. A second insulating polymer film may be applied over the conductive elements and first polymer film. The conductive elements may be made of metals, conductive polymers, or other conductive materials. Some flexible circuits may include multiple alternating layers of elements and insulating film. The transducer elements may be embedded in the alternating layers of elements and insulating film. In other embodiments, the transducer elements may be mounted (e.g., solder, adhesive, or combination thereof) to a surface of the flexible circuit and electrically coupled to one or more elements of the flexible circuit. Examples of transducer elements included in and/or coupled to a flexible printed circuit are described in International Application PCT/US2008/005619, filed May 1, 2008 and International Application PCT/GB2010/001569 filed Aug. 19, 2010.

In some embodiments, the flexible circuit including the transducer elements may be mounted on a flexible support (e.g., thin metal sheet, rubber) to form a continuously flexible array. Examples of flexible arrays mounted to flexible supports are described in U.S. Pat. No. 5,680,863, issued Oct. 28, 1997 and U.S. Pat. No. 5,735,282, issued Apr. 7, 1998. In some embodiments, the transducer elements may be included in an elastomeric material and coupled to a flexible circuit adjacent to the elastomeric material. In some embodiments, the transducer elements may be coupled to a remote circuit by flexible conductive traces.

The piecewise flexible array 205 illustrated in FIG. 2B may include multiple sub-arrays 220. These sub-arrays 220 may be rigid or semi-rigid and include one or more transducer elements (not shown). The sub-arrays 220 may be coupled by a flexible printed circuit and/or an elastomeric substrate (not shown) to form a piecewise flexible array 205. In some embodiments, the sub-arrays 220 may be conventional ultrasound transducer arrays. An example of a piecewise flexible array is described in U.S. Pat. No. 8,649,185, issued Feb. 11, 2014. In some embodiments, each sub-array 220 may have its own microbeamformer (not shown). In some embodiments, one or more sub-arrays 220 may be coupled to a microbeamformer. The microbeamformer may be integrated with the sub-array 220 or attached to the sub-array 220 (e.g., wires, solder, wireless communication). In some embodiments, one or more sub-arrays 220 may further include a microbeamformer that integrates signals from two or more microbeamformers from one or more sub-arrays 220. The microbeamformers may be implemented as rigid and/or flexible circuits.

In a conventional, rigid transducer array, the distance and orientation of each transducer element relative to other transducer elements in the array is fixed. In a flexible transducer array, the distance and/or orientation of the transducer elements relative to each other may change depending on the contour of a surface to which the flexible transducer array is applied. The relationships between the transducer elements in the array may be needed for accurate beamforming by the microbeamformer and/or beamformer 22.

In some embodiments, the flexible transducer array may include strain sensors. The strain sensors may detect the magnitude and direction of flex of different portions of the flexible array. The data from the strain sensors may be used by the ultrasound imaging system 10 to determine the position and orientation of the flexible array and the individual transducer elements. For example, as described above, the piecewise flexible array 205 may include multiple rigid sub-arrays 220, each with one or more transducer elements. The piecewise flexible array 205 may include strain sensors 215 between each rigid sub-array 220. The strain sensors 215 may provide a voltage, resistance, current and/or other signal that varies based, at least in part, on an angle between two sub-arrays 220. The strain sensors 215 may be included in a flexible circuit in some embodiments. The individual transducer elements on each sub-array 220 may have fixed relationships to one another, and the strain sensors 215 may allow an ultrasound imaging system 10 to determine the position and orientation of the sub-arrays 220 to one another for beamforming and/or other purposes.

In some embodiments, the flexible transducer array may include radio frequency ID tags and/or other tags detectable by an electromagnetic field to determine the orientation of the flexible transducer array. Based on the detected locations of the tags, the ultrasound imaging system 10 may interpolate the locations and orientations of individual transducer elements of the flexible transducer array. For example, the continuously flexible array 200 may include a plurality of regularly spaced tags 210 and the ultrasound imaging system 10 may include an electromagnetic tracking system (e.g., PercuNav system, not shown). The electromagnetic tracking system may include a field generator (not shown) which radiates an electromagnetic field that permeates the site of the flexible transducer array. The tags 210 may interact with the electromagnetic field and produce signals used to calculate the position and orientation of the tags 210. The calculated position and orientation of the tags 210 may in turn be used to determine the position and orientation of the transducer elements. The calculations may be done by a coordinate generator of the electromagnetic tracking system in some embodiments. The calculated position and orientation of the transducer elements may be used for beamforming and/or other purposes. Although shown on the continuously flexible array 200, the tags 210 and electromagnetic tracking system may be used with the piecewise flexible array 205.

Other methods of determining the location and orientation of the transducer elements in the flexible array may also be used. For example, analysis of the speckle of an ultrasound signal may provide information on the position and orientation of transducer elements relative to one another. In another example, optical sensing methods may be used to determine the contour of the flexible array.

A gel may be applied to a surface of the flexible transducer array proximate a surface of an object to be imaged and/or gel may be applied to the surface of the object. The gel may facilitate acoustical coupling between the flexible transducer array and the object. Air bubbles may exist within the gel and/or may be introduced during placement of the flexible transducer array on an object. Air bubbles may strongly reflect ultrasound waves, introducing artifacts into an acquired signal and/or interfering with delivery of an ultrasound signal to the object. In a traditional ultrasound probe, a sonographer's force on the array may be adequate to remove air bubbles from the area between the transducer array and the surface of the object. The air bubbles may be pushed with excess gel from below the transducer array to an edge of the ultrasound probe. In embodiments including a flexible transducer array with a large surface area, it may be impractical to push air bubbles from the interior of the transducer array to the periphery. The flexible transducer array may include structures to guide air bubbles to the edge of the array and/or trap air bubbles in portions of the transducer array that do not include transducer elements.

Figure 3:
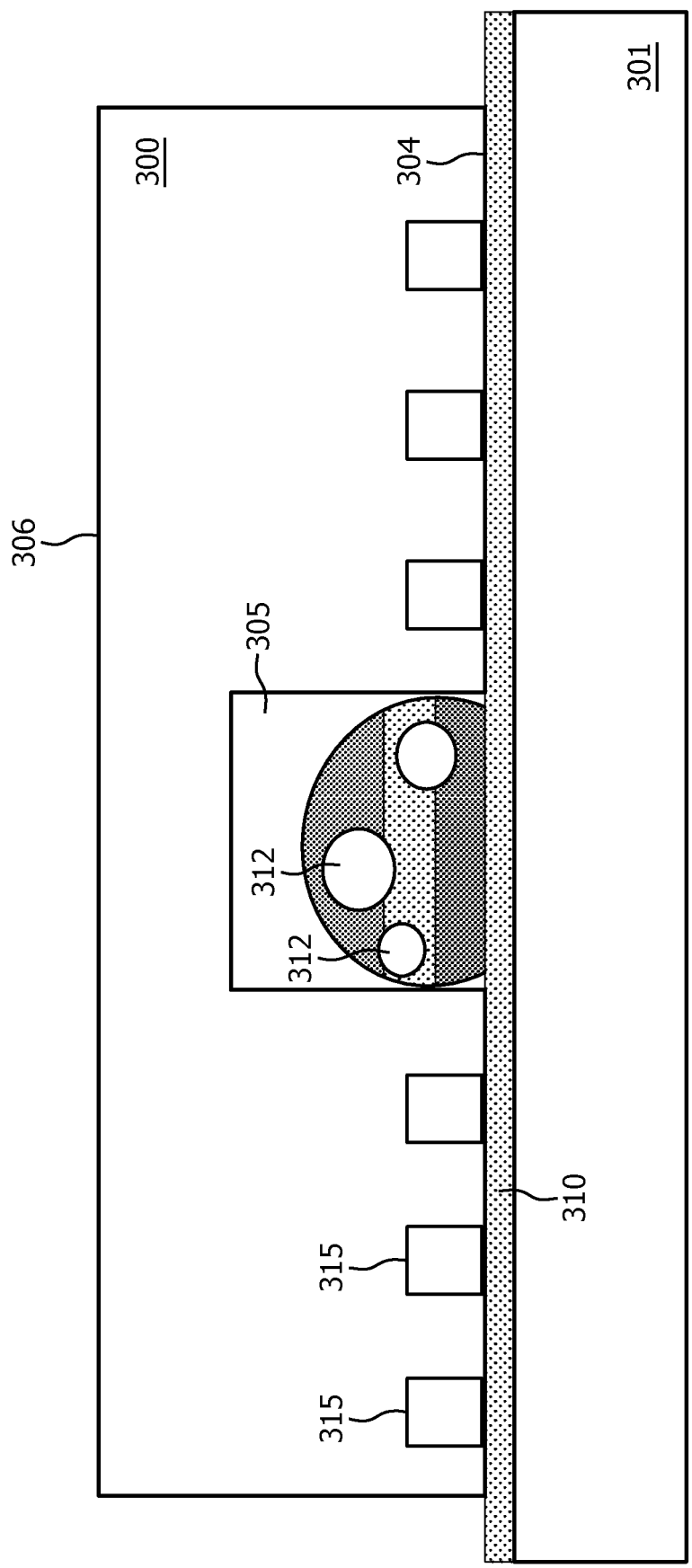
FIG. 3 is an illustration of a transducer array according to an embodiment of the disclosure.

FIG. 3 is a side-view of a flexible transducer array 300 according to an embodiment of the disclosure. The flexible transducer array 300 may be a continuously flexible array or a piecewise flexible array. The flexible transducer array 300 may have a surface 304 that is proximate an object 301 to be imaged and a surface 306 that is opposite the surface 304 and distal to the object 301. The flexible transducer array 300 may be placed on an object 301 with a layer of gel 310 between the surface 304 of the flexible transducer array proximate to the object 301. The flexible transducer array 300 may include one or more channels 305 to guide excess gel 310 and/or air bubbles 312 away from the areas of the transducer array 300 that include transducer elements 315. The channel 305 may guide air bubbles to the periphery of the array and/or retain the air bubbles 312 away from the transducer elements 315. Although shown as having a rectangular profile in FIG. 3, the channels 305 may have profiles that are rounded, triangular, and/or other shape.

In addition to applying a gel, maintaining a force on the transducer array against the surface of the object may also facilitate acoustical coupling. The force may reduce or eliminate movement of the transducer array during operation. This may improve the quality of images acquired by the transducer array and/or treatment provided by the transducer array. A transducer positioning device may be used to maintain the force against and/or the position of the flexible transducer array. The device may include an inflatable bladder and a strap. Continuing with the previous example, the EMT may apply the flexible transducer array to the victim then place the inflatable bladder across the distal surface of the flexible transducer array. The EMT may then secure a strap around the patient and the bladder. Once the strap is secured, the EMT may inflate the bladder until the desired force is applied to the flexible transducer array.

Figure 4:
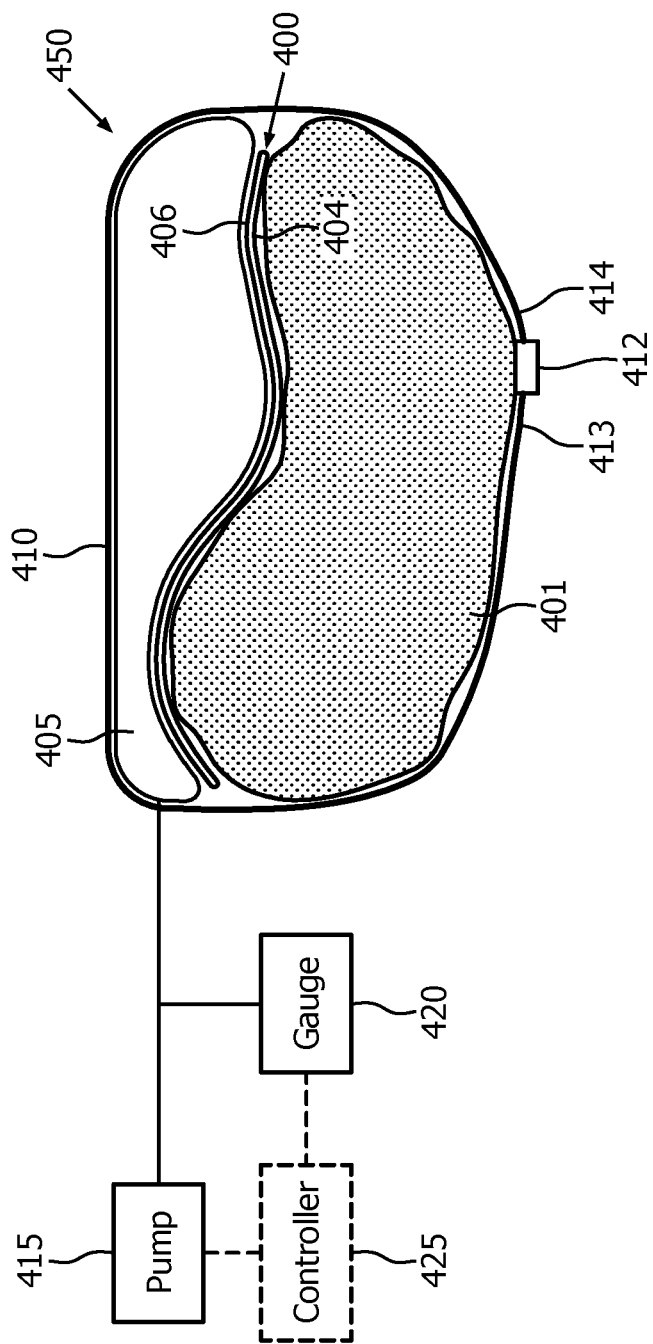
FIG. 4 is a block diagram of a transducer positioning device according to an embodiment of the disclosure.

FIG. 4 is a block diagram of a transducer positioning device 450 according to an embodiment of the disclosure. The transducer positioning device 450 may include a bladder 405 and a strap 410. In some embodiments, the bladder 405 is coupled to the strap 410. For example, the strap 410 may include two pieces of fabric sewn together, and the bladder 405 may be sewn in between the two pieces of fabric (not shown in FIG. 4). In some embodiments, the bladder 405 may be adhered to the strap 410 by an adhesive. In some embodiments, the bladder 405 and strap 410 are independent components applied separately to a flexible transducer array 400 and object 401. The flexible transducer array 400 may be a continuously flexible or piecewise flexible array. The flexible transducer array 400 may include a surface 404 proximate the object 401 and a surface 406 distal to the object 401. In some embodiments, the bladder 405 may directly contact the distal surface 406 of the transducer array 400 as shown in FIG. 4.

The strap 410 may comprise an elastic (e.g., neoprene, spandex) or inelastic material. The strap 410 may include a fastener 412 which may facilitate placement and removal of the strap 410. The fastener 412 may couple two ends 413, 414 of the strap 410. Examples of suitable fasteners include, but are not limited to, metal snaps, buttons, Velcro, buckles, and hook-and-eyelet closures. A further example of a suitable fastener includes a loop coupled to one end of the strap 410. The opposite end of the strap 410 may pass through the loop and be folded back along the strap and secured (e.g., Velcro, snaps). The fastener may be similar to the fastener of a blood pressure cuff. In some embodiments, the strap 410 may have multiple fasteners to allow the strap to be lengthened or shortened, based at least in part, on the size of the object 401. In some embodiments, the strap 410 may be continuous, and the fastener 412 may be omitted. In some embodiments, the strap 410 may not completely encircle the object 401. Instead, the strap 410 may be secured to the surface of the object 401. For example, the strap 410 may include adhesive pads (not shown) for securing the strap 410 to the object 401.

The elasticity of the strap 410 may be selected to secure the bladder 405 to the flexible transducer array 400 while allowing movement of the object 401. For example, if the flexible transducer array 400 is on a patient's torso, the elasticity of the strap 410 may allow for expansion and contraction of the torso as the patient breathes while still maintaining a force on the transducer array 400. In some embodiments, the strap 410 and/or fastener 412 may be configured to break and/or decouple when a strain over a threshold is applied. This may prevent overfilling of the bladder 405 and/or application of excessive force to the object 401. In some embodiments, the strap 410 may apply adequate force so that the bladder 405 may be omitted.

The bladder 405 may comprise an elastomeric material (e.g. rubber, latex) that is impermeable to a fluid. The bladder 405 may be inflated with a fluid, such as a liquid and/or a gas to apply a force to the flexible transducer array 400. The bladder 405 may apply an evenly distributed force to the surface 406 of the transducer array 400 distal to the object 401. In some embodiments, the force may be normal to the surface of the object 401. The bladder 405 may be inflated and/or deflated by a pump 415 coupled to the bladder 405. The pump 415 may be a manual pump operated by a user. In some embodiments, the pump 415 may be electric. In some embodiments, the pump 415 may be replaced by a compressed gas cylinder that may be used to inflate the bladder 405. The transducer positioning device 450 may include a gauge 420, which may measure and display the pressure of the fluid in the bladder 405. A user may use the pump 415 to inflate the bladder 405 to a desired pressure by observing the gauge 420.

In some embodiments, the gauge 420 may be omitted. For example, the EMT may operate the pump 415 until an adequate image is viewed on a display of an ultrasound imaging system (not shown in FIG. 4) without regard to the specific pressure of the bladder 405.

Optionally, the transducer positioning device 450 may include a controller 425 coupled to the pump 415 and gauge 420. The controller 425 may monitor the pressure indicated by the gauge 420 and operate the pump 415 to maintain the bladder 405 at a desired pressure. In embodiments where the pump 415 is replaced by a compressed gas cylinder, the gauge 420 may be replaced, or augmented with, a regulator coupled to the compressed gas cylinder.

In some embodiments, the transducer positioning device 450 may be integrated with the flexible transducer array 400. That is, the bladder 405 and/or strap 410 may be coupled to the flexible transducer array 400. This may allow a user to position and secure the transducer array 400 without assembly of multiple components. In some embodiments, one or more edges of the transducer array 400 may be coupled to the strap 410. In some embodiments, a portion of the bladder 405 in contact with the transducer array 400 may be attached to the transducer array 400 (e.g., epoxy, sonic welding).

In some embodiments, the strap 410 may be omitted from the transducer positioning device 450. For example, the flexible transducer array 400 may be positioned below the object 401 rather than above the object as illustrated in FIG. 4. The bladder 405 may be positioned below the flexible transducer array 400. In this configuration, the weight of the object 401 may be sufficient to maintain the position of the flexible transducer array 400 and bladder 405. The bladder 405 may maintain uniform force across the transducer array 400. For example, a hospital patient may be lying on her back over the transducer array and bladder. The bladder may at least partially compensate for the curvature of the patient's back.

A flexible transducer array and transducer positioning device, such as those described in reference to FIG. 4, may be used in monitoring applications. For example, a patient may be continuously imaged during a medical procedure (e.g., catheterization, biopsy). For example, a clinician may apply the flexible transducer array and transducer positioning device prior to a needle biopsy. The clinician may be able to manipulate the biopsy needle and/or other instruments without using one or more hands to maintain the position of the transducer array. In another example, a patient's blood flow in one or more blood vessels may be monitored over time to assess a condition of the patient. In a further example, the array may be coupled to a patient to allow imaging of a vein for central line placement.

In some embodiments, a conventional rigid and/or semi-rigid transducer array may be used with a transducer positioning device such as the transducer positioning device described in reference to FIG. 4. The conventional transducer array may be used for imaging and/or non-imaging applications. For example, a conventional transducer array may be applied to a maternity patient's abdomen to monitor fetal heartbeat over time.

Figure 5:
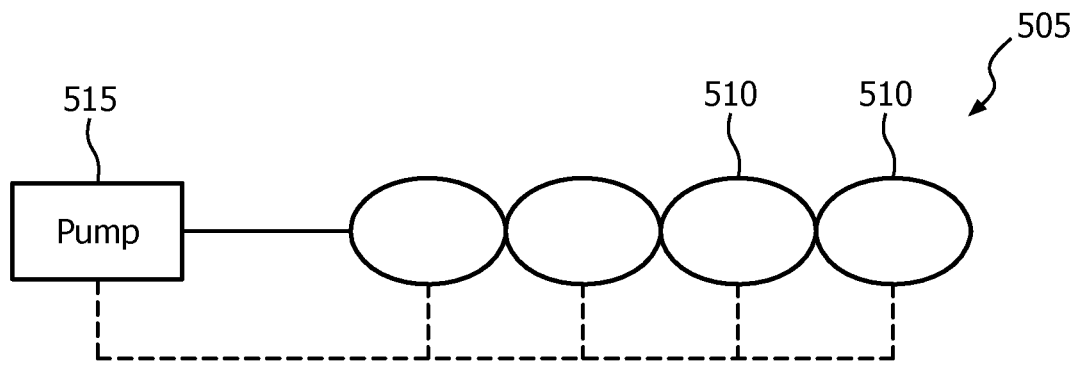
FIG. 5 is a block diagram of a bladder according to an embodiment of the disclosure.

FIG. 5 is a block diagram of a bladder 505 according to an embodiment of the disclosure. The bladder 505 may be used to implement bladder 405 shown in FIG. 4. The bladder 505 may include multiple compartments 510 that may be inflated with a fluid. The compartments 510 may be fluidly coupled so that the compartments 510 may be inflated simultaneously by a pump 515. In some embodiments, the compartments 510 may be fluidly isolated and individually coupled to the pump 515 so that the compartments 510 may be selectively inflated as illustrated by the dotted lines in FIG. 5.

Figure 6:
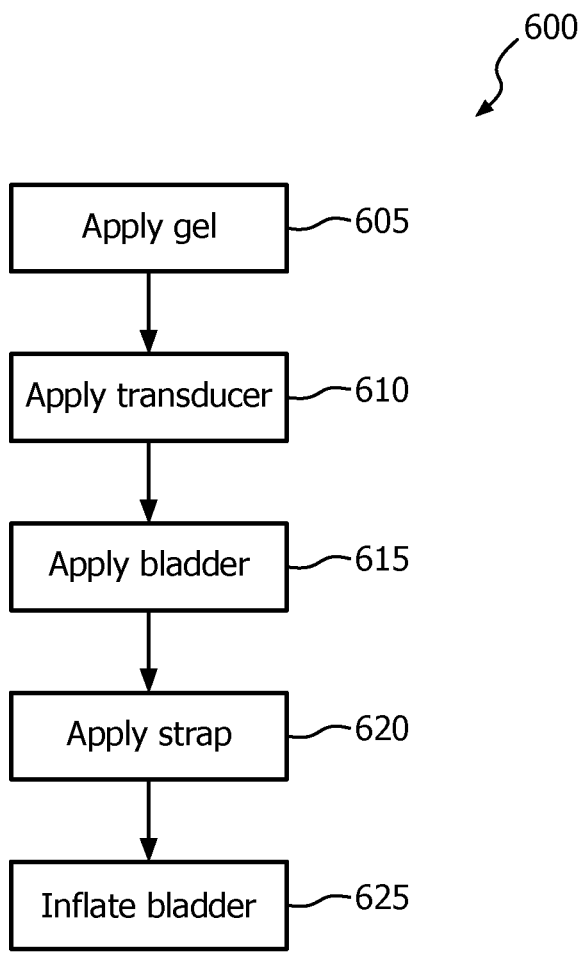
FIG. 6 is a flow chart of a method according to an embodiment of the disclosure.

FIG. 6 is a flow chart of a method 600 according to an embodiment of the disclosure. The method 600 may be used to apply a flexible transducer array to a surface of an object to be imaged. At Step 605, a gel is applied to either the surface of the object or a surface of the transducer array proximate the object. In some embodiments, the flexible transducer array may already be coated with the gel, and Step 605 may be omitted. For example, the flexible transducer array may come prepackaged with gel applied. The flexible transducer array is applied to the surface at Step 610. A bladder is applied to a surface of the transducer distal to the object at Step 615. At Step 620, a strap is applied over the bladder and around the object. In some embodiments, the bladder, strap, and/or transducer array are coupled so that Steps 610, 615, and/or 620 may be performed concurrently. After the strap has been applied, the bladder is inflated at Step 625. The flexible transducer array may then be used to acquire an image and/or apply ultrasound therapy.

Figure 7:
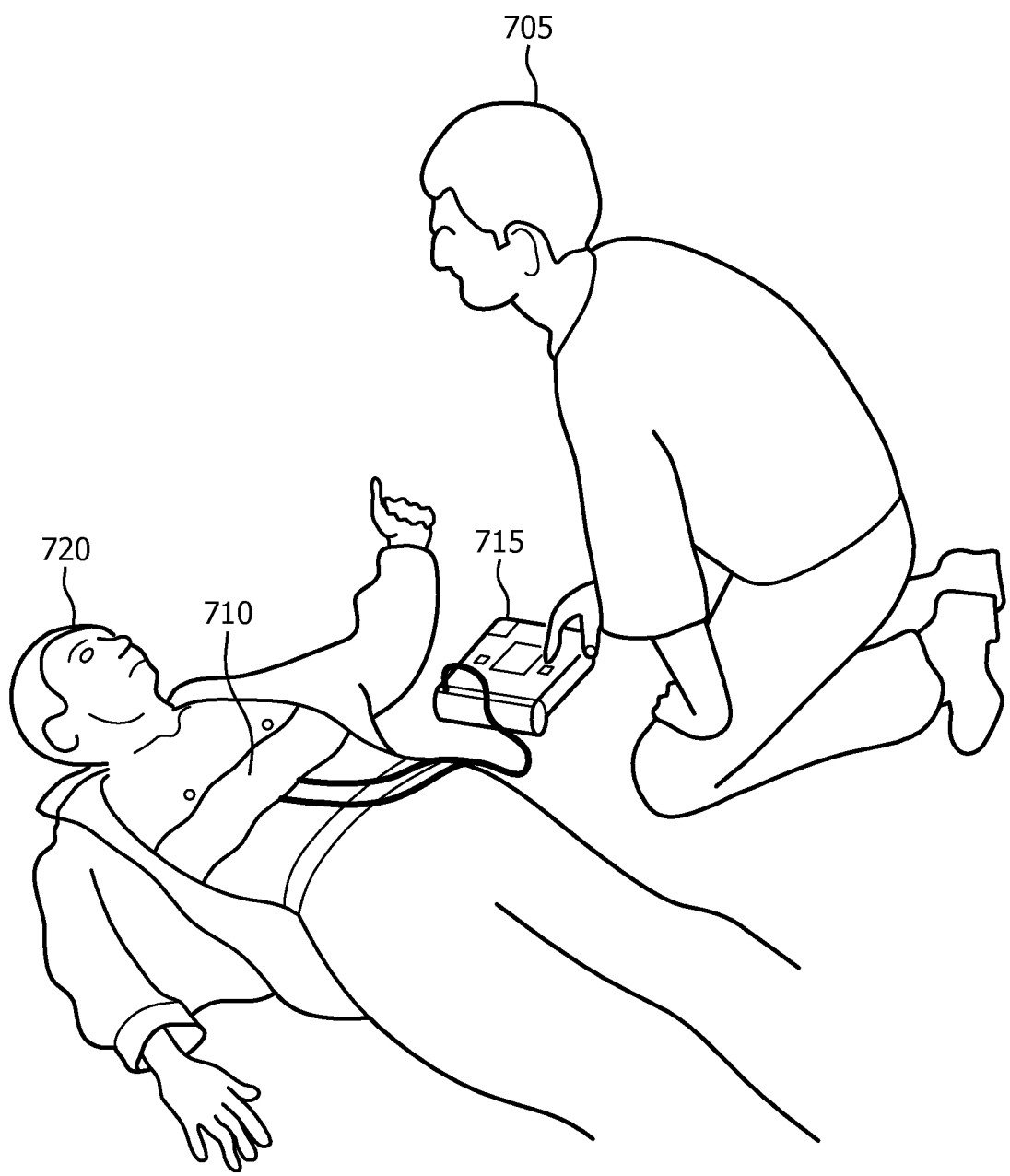
FIG. 7 is a schematic illustration of an ultrasound imaging system according to an embodiment of the disclosure.

FIG. 7 is a schematic illustration of an operator 705 using a transducer positioning device 710 including flexible transducer array (not shown) and an ultrasound imaging system 715 according to an embodiment of the disclosure. The operator 705 (e.g., EMT, physician, sonographer) may perform a method, such as method 600 shown in FIG. 6 to apply a flexible transducer array to a patient 720. In some embodiments, the ultrasound imaging system 715 may be a portable imaging system as shown in FIG. 7 or it may be a non-portable system. The ultrasound imaging system 715 may include a pump (not shown) for inflating a bladder of the transducer positioning device 710 in some embodiments. In some embodiments, the pump may be separate from the ultrasound imaging system 715. The ultrasound imaging system 715 may be coupled to the transducer array by a cable as shown in FIG. 7, however in some embodiments, the ultrasound imaging system 715 may communicate wirelessly with the transducer array.

Certain additional advantages and features of this invention may be apparent to those skilled in the art upon studying the disclosure, or may be experienced by persons employing the novel apparatus, system, and method of the present invention, chief of which is a more consistent acoustical coupling between a flexible transducer array and a surface. Another advantage of the present systems and method is that conventional medical image systems can be easily upgraded to incorporate the features and advantages of the present systems, devices, and methods.

Of course, it is to be appreciated that any one of the above embodiments or processes may be combined with one or more other embodiments and/or processes or be separated and/or performed amongst separate devices or device portions in accordance with the present systems, devices and methods.

Finally, the previous discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound system comprising:
   a flexible transducer array comprising a first surface and a second surface opposite the first surface, wherein the second surface configured to be pressed against an object to be imaged, wherein the flexible transducer array further comprises:
      a plurality of array portions configured to transmit ultrasound signals and receive echo signals and configured to be arranged in different positions and different orientations relative to one another when the second surface is pressed against the object; and
      a plurality of position and orientation detectors configured to provide indications of the different positions and the different orientations, wherein each of the plurality of position and orientation detectors comprises at least one of a strain sensor or a tag;
   a beamformer coupled to the flexible transducer array, wherein the beamformer is configured to use the indications of the different positions and the different orientations for beamforming associated with control of the plurality of array portions to transmit the ultrasound signals and to receive the echo signals;
   a transducer positioning device configured to maintain a position of the flexible transducer array against the object, wherein the transducer positioning device comprises:
      a bladder adjacent to the first surface of the flexible transducer array and configured to be inflated to press the second surface of the flexible transducer array against the object; and
      a strap configured to maintain the bladder in contact with the first surface of the flexible transducer array,
   wherein the second surface of the flexible transducer array comprises a recess located between two of the plurality of array portions, wherein, when the bladder presses the second surface of the flexible transducer array against the object, the recess is configured to receive at least one of air bubbles or excess ultrasound gel disposed between the second surface and the object.

2. The system of claim 1, further comprising a pump coupled to the bladder, the pump configured to inflate the bladder with a fluid.

3. The system of claim 2, further comprising a gauge coupled to the bladder, the gauge configured to determine a pressure of a fluid.

4. The system of claim 3, wherein the bladder comprises a plurality of compartments configured to be inflated by a fluid.

5. The system of claim 4, wherein the plurality of compartments are in fluid communication with one another.

6. The system of claim 1, further comprising:
a pump configured to inflate the bladder with a fluid; and
a controller coupled to the pump and configured to control the pump to inflate the bladder to a desired pressure.

7. The ultrasound system of claim 1,
further comprising an electromagnetic field generator,
wherein each of the plurality of position and orientation detectors comprises the tag,
wherein the electromagnetic field generator is configured to generate the indication provided by the tag.

8. The ultrasound system of claim 1, wherein the flexible transducer array is continuously flexible.

9. The ultrasound system of claim 1, wherein the flexible transducer array is piecewise flexible.

10. The ultrasound system of claim 1, wherein the strap comprises a fastener configured to secure the strap to an object.

11. The ultrasound system of claim 10, wherein the fastener is configured to release when a force on the strap exceeds a threshold.

12. The system of claim 1, wherein the strap comprises an elastic material.

13. A method comprising:
applying a second surface of a flexible ultrasound transducer array to an object to be imaged, wherein the flexible ultrasound transducer array comprises:
a first surface;
a second surface opposite the first surface;
a plurality of array portions configured to transmit ultrasound signals and receive echo signals; and
a plurality of position and orientation detectors, wherein each of the plurality of position and orientation detectors comprises at least one of a strain sensor or a tag,
wherein the second surface comprises a recess located between two of the plurality of array portions;
applying a bladder adjacent to the first surface of the ultrasound transducer array;
applying a strap to the bladder such that the bladder is maintained in contacted with the first surface of the flexible ultrasound transducer array;
pressing the second surface of the flexible ultrasound transducer array against the object by inflating the bladder such that:
the plurality of array portions are arranged in different positions and different orientations relative to one another;
the recess receives at least one of air bubbles or excess ultrasound gel disposed between the second surface of the flexible ultrasound transducer and the object;
controlling the plurality of array portions to transmit ultrasound signals and to receive echo signals, wherein the controlling includes beamforming using indications of the different positions and the different orientations provided by the plurality of position and orientation detectors.

14. The method of claim 13, further comprising applying the ultrasound gel to the object prior to applying the second surface of the flexible ultrasound transducer array to the object.

15. The method of claim 13, further comprising generating an image with the echo signals.

* * * * *